United States Patent [19]

Kölble

[11] Patent Number: 5,108,567
[45] Date of Patent: Apr. 28, 1992

[54] ELECTROPHORESIS METHOD AND APPARATUS WITH ORTHONGONAL FIELD

[75] Inventor: Konrad Kölble, Oxford, United Kingdom

[73] Assignee: Medical Research Council, London, England

[21] Appl. No.: 656,064

[22] PCT Filed: Nov. 2, 1989

[86] PCT No.: PCT/GB89/01314
§ 371 Date: Feb. 27, 1991
§ 102(e) Date: Feb. 27, 1991

[87] PCT Pub. No.: WO90/05017
PCT Pub. Date: May 17, 1990

[30] Foreign Application Priority Data

Nov. 2, 1988 [GB] United Kingdom ............... 8825625

[51] Int. Cl.$^5$ ............................................ G01N 27/26
[52] U.S. Cl. ......................... 204/180.1; 204/183.1; 204/299 R
[58] Field of Search ............. 204/180.1, 183.1, 299 R

[56] References Cited

U.S. PATENT DOCUMENTS

| | | | |
|---|---|---|---|
| 3,423,306 | 1/1969 | Hurwitz et al. | 204/299 R |
| 3,520,793 | 7/1970 | Kolin | 204/299 R |
| 3,930,982 | 1/1976 | Batha et al. | 204/299 R |
| 4,693,804 | 9/1987 | Serwer | 204/299 R |
| 4,740,283 | 4/1988 | Laas et al. | 204/299 R |

FOREIGN PATENT DOCUMENTS 256737 2/1988 European Pat. Off. .

*Primary Examiner*—John Niebling
*Assistant Examiner*—David G. Ryser
*Attorney, Agent, or Firm*—Nixon & Vanderhye

[57] ABSTRACT

A pulsed field electrophoresis method and apparatus for the separation of molecules wherein a fixed polarity potential difference between an anode and a cathode, disposed at respective opposed edges of the gel, produces a fixed polarity electric field in the plane of the gel; and simultaneously, a second set of electrodes, disposed on each side of the gel, and between which an alternating polarity potential difference is applied, produce an alternating polarity electric field orthogonal to the plane of gel. The combination of the fixed polarity and alternating electric polarity fields give unprecedented resolution in the separation of molecules across a wide range of molecular sizes.

10 Claims, 3 Drawing Sheets

ELECTROPHORESIS METHOD AND APPARATUS WITH ORTHONGONAL FIELD

The invention relates to an electrophoresis method and apparatus which may be used in conjunction with conventional electrophoretic media, such as agarose gels, for the separation of large molecules, and in particular large DNA fragments.

In conventional electrophoretic techniques, DNA molecules above a certain length display uniform velocity and therefore are not resolved. As early as 1982 it was shown that large DNA fragments can be separated, according to size, in conventional agarose gels by applying periodically alternating electric field vectors (Schwartz et al., 1982; Schwartz and Cantor, 1984). Several different pulsed field systems now achieve resolution of DNA fragments in the range 50 kilobases to at least 12.6 megabases (Mb) (Orbach, 1988). Whilst the theoretical basis for large fragment separation by pulsed field systems remains largely speculative it is thought that the pulsed field systems obtain this separation by forcing the molecules to reorient cyclically. The available systems vary considerably in their box design, gel dimensions, electrode configuration, pulsing algorithm, run time requirements, separation power, inter-lane comparability, ease of handling, and versatility (Cantor et al., 1988).

The pulsed field systems of the prior art may be divided into two types. The first type comprises systems in which the electric field vectors of the pulsed field system are oriented in a single plane defined by the agarose gel. In such systems, the separation of molecules in each lane of the gel is achieved by the alternating electric fields forcing the molecules to reorient cyclically within the plane of the gel. The gel, supported within a gel tank, is generally oriented with the plane of the gel horizontal, and two sets of electrodes positioned at a predetermined angle.

Examples of such systems include orthogonal field agarose gel electrophoresis (OFAGE), horizontal and vertical field inversion gel electrophoresis (FIGE), rotating gel/electrode electrophoresis (RGE/REE), and contour-clamped homogeneous electric field gel electrophoresis (CHEF) and its variants, e.g. programmable, autonomously controlled electrode gel electrophoresis (PACE).

OFAGE is the archetypal system using either mixed uniform/non-uniform or non-uniform field configurations (Schwartz and Cantor, 1984; Van Ommen and Verkerk, 1986). It suffers, however, from marked distortion of the outer lanes of the gel, thereby limiting the area of the gel usable for the sizing of molecules and inter-sample comparison, to a few central lanes.

FIGE is a system based on reversing the polarity between only two parallel electrodes at either end of the gel and creating a net movement by using non-identical forward and reverse pulse times in each cycle (Carle et al., 1986). It is capable of producing straight lanes on large gels. However, the 180 degree angle between pulse vectors results in unacceptable broadening of bands on prolonged runs and thus compromises resolution, especially of large molecules. In the vertical variant of this system, the vertical orientation of the plane of the gel ensures more effective cooling of the gel than in the horizontal variant (Dawkins et al., 1987). The vertical system still suffers, however, from the inherent broadening of bands and low resolution of FIGE.

RGE/REE are systems in which either a circular gel or a single pair of electrodes are periodically rotated with respect to the other (Serwer, 1987; Southern et al., 1987). The molecules to be separated are thus exposed alternately to two uniform electric fields at a fixed angle. Although the systems give straight lanes over a fairly large area, their major drawback lies in their reliance on moving parts, which, given the long run times and extended day to day use, makes them liable to mechanical breakdown.

CHEF is a system based on a hexagonal array of up to 24 electrodes clamped to predetermined electric potentials (Chu et al., 1986; Vollrath and Davis, 1987). This design and its variants (Clark et al., 1988; Birren et al., 1988) involve the most complex electrode configuration and electronic controls to separate molecules in gels up to 13 cm × 13 cm. The resolution achieved is not superior the RGE system. Distortion in the outerlanes restricts the number of usable lanes.

The second type of system comprises systems in which use is made of the third dimension of the gel, i.e. orthogonal to the plane of the gel.

The prototype of such a system is transverse alternating field electrophoresis (TAFE) (Gardiner et al., 1986; Laas et al. 1988). This system employs two pairs of alternately activated electrodes positioned to provide alternate electric fields intersecting at an angle of 115 degrees. A vertically suspended gel is positioned where the alternate fields intersect so as to bisect the angle at which the fields intersect.

The system exposes all the lanes of the gel medium to identical field conditions during the run and achieves sharp bands. A major drawback, however, is that the restriction on inter-electrode distance, imposed by keeping the interelectrode potential and tank dimensions within manageable margins, allows only for a gel of relatively small length, i.e. separation distance, typically 10 cm (Laas et al., 1988). Such a gel is too small to yield competitive resolution.

A particular drawback of the known pulsed field electrophoresis systems is that whilst they may achieve some measure of separation of large molecules, in so doing small molecules are not resolved. This simultaneous separation of small and large molecules has not been possible to date.

According to a first aspect of the present invention there is provided an electrophoresis apparatus comprising first electrode means consisting of a cathode and an anode and means for supplying a fixed polarity potential difference to said cathode and said anode, and gel retaining means suitable, in use, to retain a gel within said apparatus such that, in use, the said anode and said cathode are disposed at respective opposed edges of said retained gel to produce a fixed polarity electric field in the plane of said retained gel, characterised in that said apparatus further comprises second electrode means comprising at least two electrodes and means for supplying an alternating polarity potential difference to said electrodes, at least one of said electrodes being disposed on each side of the plane of said retained gel such that in use said second electrode means produce an alternating polarity electric field intersecting and substantially orthogonal to the plane of said retained gel.

The apparatus of the present invention is used contained within a gel tank. Said gel tank is preferably of conventional design comprising an open-topped rectangular box made of an electrically insulating material such as glass, Plexiglass or Perspex. Said gel tank is filled with an electrophoresis buffer solution. Preferably the electrophoresis buffer solution is a conventional electrophoresis buffer solution. Advantageously, said gel tank is provided with means for circulating, and thermostatically controlling the temperature of, said buffer solution.

Said retained gel may consist of any electrophoretic gel capable of allowing transport of large molecules. Typically said retained gel is an agarose gel. Agarose gels are typically cast between glass plates with sample wells formed by insertion of a well former in the cassette before said agarose gel solidifies. Samples of molecules for 2 electrophoresis may be loaded onto said agarose gel in agarose blocks before immersing said agarose gel in said buffer solution. Alternatively, said samples may be loaded onto said agarose gel as solutions after immersing said agarose gel in said buffer solution.

Said gel retaining means may comprise any conventional means for retaining and supporting said retained gel in said gel tank. Preferably, said retained gel is retained, within said gel tank, in a vertical orientation by securing, by suitable means, the respective top and bottom horizontal edges of said retained gel. Optionally, said retained gel may be additionally secured and supported by removable glass bars adjacent the respective vertical edges of said retained gel. If said retained gel is an agarose gel it must be retained in position against the natural buoyancy of said agarose gel in said buffer solution.

Said means for supplying a fixed polarity potential difference between said cathode and said anode may consist of a conventional power source, typically with a maximum output between 300 mA, 150 V and 2.5 A, 500 V.

Said means for supplying an alternating polarity potential difference to said electrodes may consist of a conventional power source, typically with a maximum output between 300 mA, 150 V and 2.5 A, 500 V, in conjunction with a switching unit capable of alternating the polarity of the potential difference, supplied by said power source, with a pulse time of between 0.1 seconds and at least 5000 seconds. Preferably, the switching unit is capable of alternating the polarity of the potential difference with a pulse time of between 60 seconds and 60 minutes.

Optionally, both said power sources may be the same power source.

Preferably, said means for supplying an alternating polarity potential difference comprises a power source and an electronic switching unit capable of supplying and ramping an alternating polarity potential difference with a pulse time of between 0.1 seconds and at least 5000 seconds, more preferably, between 60 seconds and 60 minutes.

Preferably, said means for supplying a fixed polarity potential comprises a power source and a unit capable of periodic ramping of said fixed polarity potential difference with a pulse time of between 0.1 seconds and at least 5000 seconds, more preferably, between 60 seconds and 60 minutes.

More preferably, said unit capable of periodic ramping of said fixed polarity difference and said electronic switching unit capable of supplying and ramping said alternating polarity potential difference are synchronisable.

Advantageously, said means for supplying said fixed polarity and alternating polarity potential differences comprise a synchronisable two function signal generator, capable of delivering voltage gradients ranging from $-150$ V to $+150$ V at currents of up to 500 mA with a pulse time of between 0.1 seconds and at least 5000 seconds, preferably, between 60 seconds and 60 minutes.

A feature of the present invention is the high versatility in pulse time and field strength parameters. Said electronic switching unit may be used to implement any pattern of alternating electric fields produced by said second electrode means; for example, linear or exponential pulse ramps, or alternating pulse times. In addition, combination of said fixed polarity and alternating polarity electric fields allows for an alternating polarity electric field off-period, whilst still providing net sample motion towards said anode. Furthermore, independent control over the fixed polarity and alternating polarity electric fields gives full control over their ratio and hence over the total effective field produced by summation of the fixed polarity and alternating polarity components. In addition the fixed/alternating polarity electric field ratio can be changed once or repeatedly during a pulse of the same polarity to generate "intrapulse" sweeps of the effective field vector. Similarly "intrapulse" voltage ramps can be implemented at a constant fixed/alternating polarity electric field ratio or on top of an "intrapulse" sweep of the effective field vector. Such "intrapulse" pulse patterns have been found to be particularly effective in achieving enhanced separation of molecules when used in combination with the apparatus of the present invention. Independent control of said fixed polarity and said alternating polarity electric fields allows minimisation of run times at any particular range of molecular sizes to be separated.

The present invention may be used to separate any large charged molecules. For example, DNA, RNA and proteins. In particular DNA of a size not less than 100 bases and up to a maximum of at least 12.6 megabases may be resolved.

A further feature of the present invention is the high resolution obtainable when molecules in both narrow and wide molecular size ranges are being separated. The apparatus may be run in either a wide range mode or focused ranged mode by selecting appropriate electric field strengths, fixed polarity/alternating polarity electric field strength ratios, pulse time and through ramping the electric field pulses. In wide range mode a broad range of molecular sizes may be separated simultaneously. The broad range may include both large molecules, separated only by pulsed field electrophoresis techniques, and small molecules, separated by conventional electrophoresis techniques but normally not resolved by pulsed field electrophoresis; for example, DNA fragments in the size range 4 kilobases to 2 megabases may be separated on a single agarose gel.

In focused range mode a specific range of molecular sizes may be expanded to give enhanced resolution. For example, within a single gel enhanced resolution of a band of DNA fragments in the range 300 to 500 kilobases may be obtained. DNA fragments outside that range will still be separated, although with lower resolution. The operational limits of the apparatus for the separation of DNA molecules extend from molecules as small as 100 bases to at least 12.6 megabases. The combined effect of the simultaneously applied fixed polarity and alternating polarity electric fields of the present invention appears to have an, as yet unexplained, condensing effect resulting in unsurpassed band sharpness and resolution.

Said anode and said cathode of said first electrode means and said electrodes of said second electrode means may comprise conventional electrophoresis electrodes of any design. In particular, they may comprise plates, wires or strips, or any suitable combination of plates and wires and strips. The material of construction of said anode, cathode and electrodes may be any suitable electrically conducting material, such as platinum or graphite. Preferably said anode, cathode and electrodes are platinum.

In use, said anode and said cathode produce a substantially homogeneous fixed polarity electric field between said cathode and said anode in the plane of said retained gel. Said fixed polarity electric field drives the molecules of said sample through said retained gel towards said anode. Simultaneously said electrodes produce an alternating polarity electric field intersecting and substantially orthogonal to the plane of said retained gel. The effect of said alternating electric field is to force said molecules to reorient in said gel in a cyclical fashion.

A feature of the present invention is that in use, the electric fields arising from the configuration of said anode, cathode and electrodes is substantially homogeneous across the width of said retained gel. This gives molecular migration which is straight and equivalent between lanes, and high resolution in the separation of molecules.

Preferably said anode, said cathode and said electrodes are wires. More preferably, said electrode means comprise four wires located parallel to said anode and said cathode, such that said four electrodes, said anode and said cathode are equally radially distributed about an axis parallel to and mid-way between said cathode and said anode. Preferably said anode, said cathode and said electrodes span the entire width of said gel tank.

A feature of the present invention is the large dimensions of said retained gel that can be accommodated by said apparatus. The maximum length of said retained gel is determined by the distance between said anode and said cathode. The maximum width of said retained gel is determined by the maximum length of said anode, cathode and electrodes across the width of said gel tank. Maximum usable gel area of said retained gel is at least 180 mm × 180 mm (length × width).

At any given volume of said gel tank the configuration of said anode, said cathode and said electrodes facilitates larger separation distances compared to other systems as the length of said retained gel is only slightly less than the distance between said anode and said cathode. The minimisation of the difference between the length of said retained gel and the distance between said anode and said cathode is especially favourable because, for a given length of said retained gel, a lower potential difference between said anode and said cathode can be used in order to achieve a given field strength. This reduces demand on the power source output and on said thermostatic buffer temperature control means.

According to a second aspect of the present invention there is provided a method of electrophoretic separation of molecules wherein said molecules, contained within a gel, are subjected to a fixed polarity electric field in the plane of said gel, and characterised in that said molecules are simultaneously subjected to an alternating polarity electric field substantially orthogonal to the plane of said gel.

Optionally, the field strengths of the fixed polarity and alternating polarity electric fields and the pulse time of the alternating polarity electric field are constant during the separation of molecules.

Alternatively, the field strengths of the fixed polarity and alternating polarity electric fields may be varied. Additionally, the pulse time of the alternating polarity electric field may be varied.

Preferably, the pulse time is ramped such that the duration of each pulse increases during the course of the separation.

Optionally, the ratio of the fixed and alternating electric fields may be constant such that the angle between the plane of the gel and the direction of the effective field vector, produced by summation of the fixed and alternating field vectors, is constant.

Alternatively, the ratio of the fixed and alternating fields may be varied such that the direction of the effective field vector is varied. Preferably, the effective field vector is varied within a single pulse. More preferably, the angle between the plane of the gel and the effective field vector is increased during the course of each pulse.

Optionally, the strength of the effective field vector is constant. Alternatively, the strength of the effective field vector may be ramped. Preferably, the strength of the effective field vector is ramped in each pulse. More preferably, the strength of the effective field vector is ramped repeatedly within a single pulse.

Preferably, said method of electrophoretic separation of molecules comprises use of an electrophoresis apparatus according to the first aspect of the present invention.

An embodiment of the present invention will now be described in more detail with reference to the drawing in which, FIG. 1 is a schematic representation of a specific embodiment of the present invention in perspective;

Figure 1:
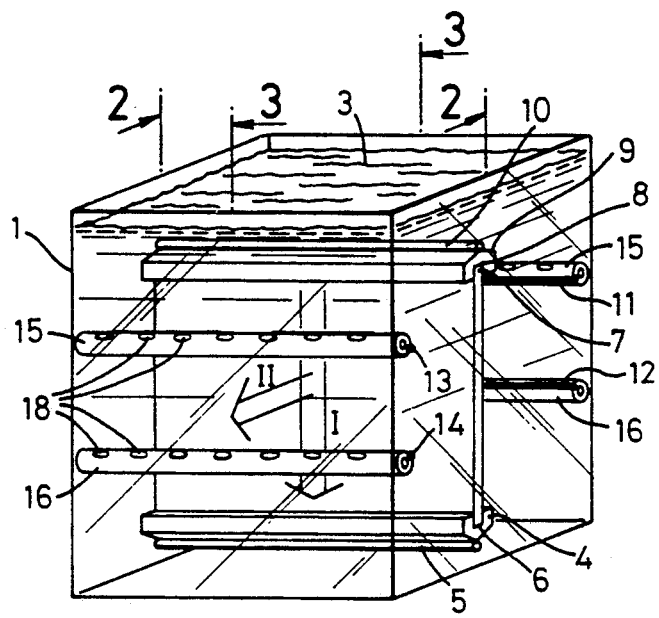

In FIG. 1 a specific embodiment of the electrophoresis apparatus of the present invention is shown incorporated in an electrophoresis gel tank denoted (1). The gel tank is illustrated containing an electrophoretic agarose gel (2), of dimension 160 mm × 150 mm × 6 mm (length × width × thickness). The gel tank is made of Perspex, and is an open-topped rectangular box of external dimensions (height × width × depth) of 195 mm × 165 mm × 260 mm. The gel tank is filled with a conventional electrophoretic buffer solution (3), for example, 0.2 × TBE buffer.

Fixed centrally along the width of the bottom of the tank (1) is anode holder (4). The anode holder is a Perspex block 9 mm × 9 mm × 150 mm. Integral with the anode holder is anode (5), spanning the width of the gel tank. Incorporated into the anode holder, and parallel to the anode, is a groove (6) into which the bottom anodal edge of the gel may be located and thereby secured and supported across the width of the tank.

The gel (2) is further secured and supported in a vertical orientation by location of the top cathodal edge (7) of the gel in a groove (8) in the underside of the removable cathode holder (9). The cathode holder (9) thus prevents upward dislocation of said gel. Preferably, the gel is additionally supported by removable glass bars at its sides. The cathode holder (9), which also comprises a Perspex block 9 mm×9 mm×150 mm, is releasably secured to the walls of the gel tank (1). Integral with the cathode holder (9) is the cathode (10), which runs parallel to the cathodal edge of the gel. Positioned, two on each side of the gel (2), are four electrodes (11-14). They are positioned equidistant from the gel (2) such that the anode (5), the cathode (10), and the four electrodes (11-14) are equally radially distributed about an axis parallel to and mid-way between the anode and the cathode. Each electrode (11-14) is held in position by a Perspex tube (15,16), 150 mm×10 mm (length×diameter), fixed to the gel tank. In the side of each Perspex tube (15,16), parallel to the longitudinal axis of each tube, is a groove, 150 mm×1 mm×1 mm (length×width×diameter), in which one of the electrodes (11-14) is located. The tubes (15,16) are oriented such that the grooves face the axis parallel to and midway between the anode and cathode. The anode, cathode and electrodes are platinum wires 0.8 mm in diameter, of a length to span the full width of the gel tank (1). The four electrode holding tubes (15,16) also act as ports for the circulation of the buffer solution by means of seven equidistantly spaced holes (18) of 2 mm diameter positioned in the top circumference of said tubes. The buffer is continually removed from the tank via the holes in the two top electrode holding tubes (15), pumped through a cooling coil thermostated by an isolated second coolant circuit, and returned to the gel tank (1) via the holes in the two bottom electrode holding tubes (16).

In an alternative arrangement, the buffer is continually removed from the tank via two T-shaped outlets, one positioned above each top electrode (11,13) on each side of the gel, pumped through two cooling coils thermostated by an isolated second coolant circuit, and returned to the gel tank (1) via two T-shaped inlets positioned one below each bottom electrode (12,14) on each side of the gel.

Figure 2:
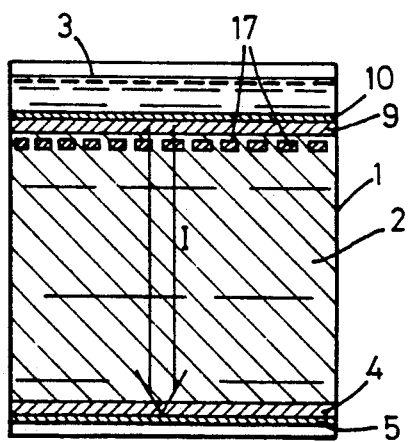
FIG. 2 is a cross-section of FIG. 1 in the plane defined by A—A.

In operation, a first power source (for example, a Model E411 power supply, supplied by Consort), of output of 500 mA and 150 V, in constant voltage mode is connected to the anode (5) and cathode (10). Thus, there is produced a fixed polarity electric field vector (I) (FIG. 2) directed at driving molecules, initially contained in wells (17) adjacent said cathode (as in conventional electrophoresis), towards the anode through the gel.

Figure 3:
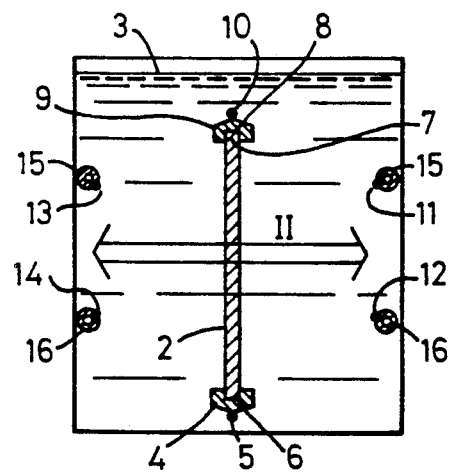
FIG. 3 is a cross-section of FIG. 1 in the plane defined by B—B.

Simultaneously, the same or a second similar power source, in conjunction with an electronic switching unit (for example, the efs/eps system supplied by Flowgen Instruments Limited) that is capable of supplying and ramping periodically inverted pulses, of pulse time between 0.1 seconds and 5000 seconds, is connected to the electrodes (11-14) such that one pole of the same or second power supply is connected to a first pair (11,12) of electrodes and the opposite pole is connected to the second pair of electrodes (13, 14). Thus, there is produced an alternating polarity electric field vector (II) (FIG. 3), periodically inverted at an angle of 180 degrees, directed between the first electrode pair (11, 12) and the second electrode pair (13, 14), substantially orthogonal to the plane of fixed polarity field (I) and of the gel (2).

Typically the fixed polarity and polarity alternating electric field strengths are in the range 0.1 V/cm to 10 V/cm. More particularly, when the invention is used in its wide range mode (for example to separate DNA molecules in the range 4 kilobases to 2 megabases) a field strength of approximately 3 V/cm may be used; when used in its focused range mode (for example to separate DNA molecules in the range 250 to 1200 kilobases) a higher field strength of approximately 7-10 V/cm may be used.

Separation of DNA molecules over 2 megabases may be enhanced by the use of a two channel function generator. For example, synchronised linear "saw-tooth" voltage ramps of 60 minutes duration may be used. Typically, the fixed polarity potential difference between the anode (5) and cathode (10) is monotonously ramped from 1 V to 50 V whilst the alternating potential difference between the first electrode pair (11,12) and the second electrode pair (13,14) is alternately and synchronously ramped from −1 V to −50 V and +1 V to +50 V.

EXAMPLE 1

Figure 4:
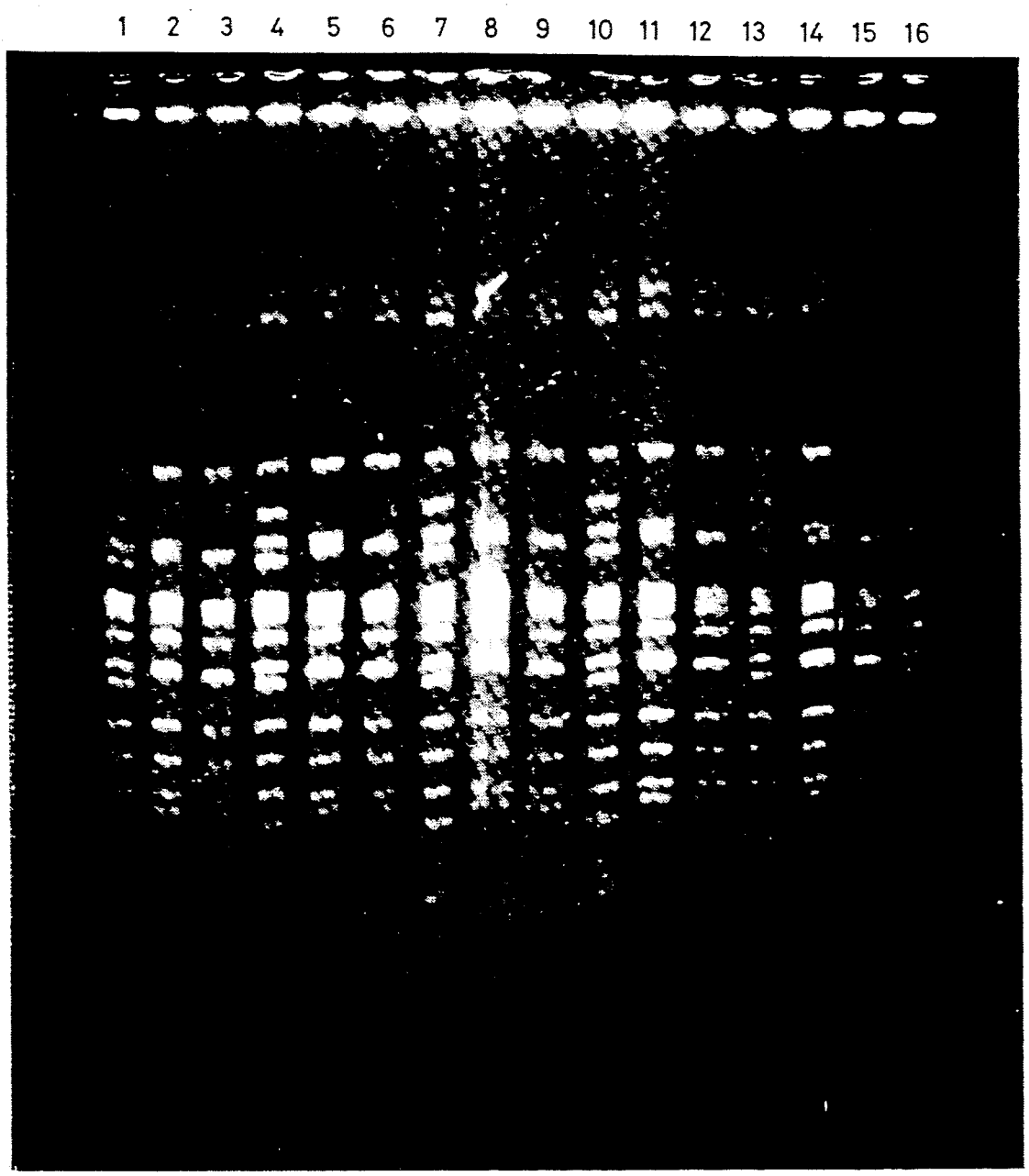
FIG. 4 illustrates the separation of chromosomes of three strains of Saccharomyces cerevisiae by an electrophoresis apparatus of the present invention.

FIG. 4 depicts the separation of the chromosomes (electrophoretic karyotype) of three different strains of Saccharomyces cerevisiae using an electrophoresis apparatus and method according to the present invention. The sample well is at the top; lanes, 1, 4, 7, 10, 13 and 16 are YP148; lanes 2, 5, 8, 11 and 14 are X2180-1B; lanes 3, 6, 9, 12 and 15 are MD40-4C. All the chromosomes (17 in YP148, 14 in X2180-1B and 13 in MD40-4C) are resolved.

In this example the following protocol was followed. The gel (160 mm×150 mm×6 mm [length×width×thickness]) consisted of 0.8% (w/v) HGT agarose (Sea-Kem Marine Colloids) dissolved in 0.2xTBE (1xTBE is 10.9 g Tris, 52 g boric acid, 0.93 g disodium EDTA per liter, pH 8.3). It was cast in a mould consisting of a spacer glass plate (150 mm×60 mm×6 mm [width−length×thickness]) clamped between two covering glass plates (150 mm×220 mm×3 mm [width×length×thickness]) laterally sealed with two strips of autoclave tape. After pouring the liquid agarose solution at approx. 50 degrees Celsius into the mould, wells for the samples were formed by inserting a plastic comb with 18 teeth (5 mm×6 mm×3 mm [width×length×thickness]), spaced 3 mm apart into the open top of the mould. The gel was left to set for 1 hr at 4 degrees Celsius.

0.2xTBE electrophoresis buffer was continuously circulated by an aquarium pump (DP35/3, supplied by Totton Electrical Products). The buffer was taken in through holes in the top pair of the circulation pipe/electrode holders (15), driven through the internal coil of a glass heat exchanger and returned into the gel tank via holes in the bottom pair (16) of the circulation pipe/electrode holders. The outer chamber of the heat exchanger was perfused with distilled water by a circulating refrigerated bath (FRIGOSTAT, supplied by DESAGA). The thermostat was set at 14 degrees Celsius yielding a buffer temperature in the gel tank of 20 degrees Celsius throughout the run.

Samples were loaded into wells as approximately 1 mm thick slices of gel inserts containing DNA of the respective strains and sealed with 1% low gelling agarose at 40 degrees Celsius. Gel inserts were prepared according to Van Ommen et al, (1986).

The fixed polarity and the alternating polarity electrodes were both energized using the two parallel output ports of a Consort E411 power pack at a constant voltage of 110 Volts yielding an initial current of 330 mA. The polarity of the alternating polarity electrode set was inverted at intervals ramped exponentially from 60 seconds to 130 seconds using a commercially available polarity switcher and software (EFS/EPS system, Flowgen Instruments Ltd.) in conjunction with an IBM compatible microcomputer. The program settings were: Active run: 48 h; Initial forward: 60 sec; Initial reverse: 60 sec; Final forward: 130 sec; Final reverse: 130 sec; Curve: D (square root).

DNA was visualized after soaking the gels in 500 ml of TBE containing 0.5 µg/ml ethidium bromide for 15 minutes. Photographs were taken using Kodak 4415 technical pan film with shortwave UV illumination. Exposure times was 2 minutes at f 4.5 with an interference contrast filter.

EXAMPLE 2

In an experiment involving intrapulse voltage ramps for the separation of DNA molecules ranging from 100 kb to over 5.6 Mb, gel casting, buffers, sample loading, and DNA visualisation procedures were as described in Example 1.

The fixed polarity and the alternating polarity electrodes were both energized using the same output port of a custom made DC-power source capable of linearly increasing the voltage from 0–150 Volts with ramp durations between 1 and 60 minutes. Any specified voltage ramp is repeated until the power source is reset to start a new ramp from 0 Volts by a low voltage signal provided via the parallel port (RS 232) of an IBM compatible microcomputer.

The maximum voltage (ramp end point) was set at 75 Volts and the ramp duration at 1 minute. The current reached 400 mA at the voltage maximum. The polarity of the horizontal electrode set was inverted at intervals ramped exponentially from 60 seconds to 3276 seconds using a custom made polarity switcher and software in conjunction with an IBM compatible microcomputer. The program settings were: Run time: 48 h; Initial pulse time: 60 sec; Final pulse time: 3276 sec; Percent of run time to reach 50% of the pulse time increase: 25%. Resetting signals to the power source were given synchronously to each reversal of the polarity.

EXAMPLE 3

In an experiment involving a changing ratio of the fixed and the alternating polarity fields administered repeatedly within a pulse of the same polarity to separate DNA molecules ranging from 200 kb to 3.5 Mb, a gel casting, buffers, sample loading, and DNA visualisation procedures were as described in Example 1.

To implement such a combination of intrapulse voltage ramping and vector sweeping, the fixed polarity and the alternating polarity electrodes were energized independently using a CONSORT E411 power pack in constant voltage mode for the fixed polarity electrodes and the custom made DC-power source specified in Example 2 for the alternating polarity set of electrodes. The fixed polarity voltage was set at 100 V resulting in an initial current of 100 mA. The maximum voltage (ramp end point) to be applied to the alternating polarity electrodes was set at 125 Volts and the ramp duration at 1 minute. The current reached 400 mA at the voltage maximum. The polarity of the alternating polarity electrodes was inverted at a constant interval of 191 seconds using a custom made polarity switcher and software in conjunction with an IBM compatible microcomputer. The program settings were: Run time: 48 h; Initial pulse time: 191 sec; Final pulse time: 191 sec. Resetting signals to the power source were given synchronously to each reversal of the polarity.

COMPARATIVE EXAMPLE 1

Figure 5:
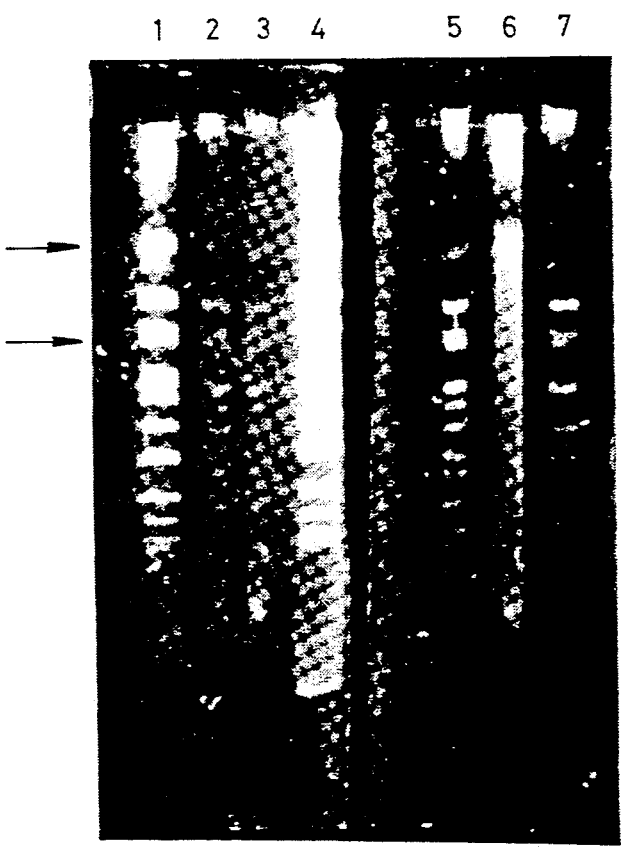
FIG. 5 illustrates the partial separation of the chromosomes of two strains of Saccharomyces cerevisiae by a TAFE electrophoresis apparatus of the prior art.

FIG. 5 depicts the partial separation of the chromosomes (electrophoretic karyotype) of two different strains of Saccharomyces cerevisiae using an electrophoresis apparatus of the TAFE design. The sample well is at the top; lanes 1 and 4 are X2180-1B; lanes 2, 3, 5 and 7 are 334. Only 12 of the 14 chromosomes of X2180-1B and 13 of the 14 chromosomes of 334 are resolved. Arrows in FIG. 5 indicate the two pairs of bands in X2180-1B which were unresolved in the present Comparative Example but which were resolved in Example 1 of the present invention.

In this comparative example the following protocol was followed.

The separation was performed on a complete BECKMAN GeneLine System following the manufacturer's instructions given in the GL-1M-1 instruction manual (January 1988). The controller was programmed with the two-stage "Program 1" as described on page 15 ff of the manual. The first stage was run at 170 mA for a total of 30 minutes with pulses every 4 seconds. The second stage was run at 150 mA for a total of 18 h with pulses every 60 seconds.

It will be understood that the invention is described by way of example only and modifications of details may be made within the scope of the invention.

REFERENCES

Birren, B. W., Lai, E., Clark, S. M., Hood, L. and Simon, M. I. (1988) Nucleic Acids Res. 7563-7581

Cantor, C. R., Smith, C. L. and Mathew, M. K. (1988) Ann. Rev. Biophys. Biophys. Chem. 17, 287-304

Carle G. F. Frank, M. and Olson M. V. (1986) Science 232, 65-68

Chu, G., Vollrath D. and Davis, R. W. (1986) Science 234, 1582-1585

Clark, S. M. Lai E., Birren, B. W. and Hood, L. (1988) Science 1203-1205

Dawkins, H. J. S., Ferrier, D. J. and Spencer, T. L. (1987) Nucleic Acids Res. 15, 3634-3635

Laas, W. A., Patterson, D. and Gardiner, K. J. (1988) U.S. Pat. No. 4,740,283.

Gardiner, K., Laas, W. and Patterson D. (1986) Somatic Cell. Mol. Genet. 12, 185-195.

Orbach, M. J., Vollrath, D., Davis, R. W. and Yanovsky, C. (1988) Mol. Cell Biol. 8, 1469-1473

Schwartz, D. C., Saffran, W., Welsh, J., Haas, R., Goldenberg, M. and Cantor, C. R. (1982) Cold Spring Harbor Symp. Quant. Biol. 47, 189-195

Schwartz, D. C. and Cantor, C. R. (1984) Cell 37, 67-75

Serwer, P. (1987) Electrophoresis 8, 301-304

Southern, E. M. Anand, R., Brown, W. R. A. and Fletcher, D. S. (1987) Nucleic Acids Res. 15, 5925-5943

Van Ommen, G. J. B. and Verkerk, J. M. H. (1986) Analysis of Human Genetic Diseases (Davies, K. E., ed.), pp. 113-133, IRL Press Vollrath, D. and Davis, R. W. (1987) Nucleic Acids Res. 15, 7865-7876.

I claim:

1. A method of electrophoretic separation of molecules wherein said molecules, contained within a gel, are subjected to a fixed polarity electric field in the plane of said gel, said fixed polarity field being produced by a first electrode means,
   characterised in that said molecules are simultaneously subjected to an alternating polarity electric field substantially orthogonal to the plane of said gel, said alternating polarity electric field being produced by a second electrode means.

2. A method of electrophoretic separation of molecules according to claim 1 wherein said molecules comprise DNA molecules.

3. An electrophoresis apparatus comprising first electrode means consisting of a cathode and an anode and means for supplying a fixed polarity potential difference to said cathode and said anode, and
   gel retaining means suitable, in use, to retain a gel within said apparatus such that, in use, the said anode and said cathode are disposed at respective opposed edges of said retained gel to produce a fixed polarity electric field in the plane of said retained gel,
   characterised in that said apparatus further comprises second electrode means comprising at least two electrodes and means for supplying an alternating polarity potential difference to said electrodes, at least one of said electrodes being disposed on each side of the plane of said retained gel such that in use said second electrode means produce an alternating polarity electric field intersecting and substantially orthogonal to the plane of said retained gel.

4. An electrophoresis apparatus according to claim 3, wherein said means for supplying an alternating polarity potential difference comprises a power source and a switching unit capable of supplying and ramping an alternating polarity potential difference with a pulse time of between 0.1 seconds and at least 5000 seconds.

5. An electrophoresis apparatus according to claim 4, wherein said means for supplying a fixed polarity potential difference comprises a power source and a unit capable of periodic ramping of said fixed polarity potential difference with a pulse time of between 0.1 seconds and at least 5000 seconds.

6. An electrophoresis apparatus according to claim 5 wherein said unit capable of periodic ramping of said fixed polarity potential difference and said switching unit capable of supplying and ramping said alternating polarity potential difference are synchronisable.

7. An electrophoresis apparatus according to claim 3 wherein said anode and said cathode of said first electrode means and said electrodes of said second electrode means are wires.

8. An electrophoresis apparatus according to claim 3 wherein said second electrode means comprises four electrodes.

9. An electrophoresis apparatus according to claim 8 wherein said four electrodes are located parallel to said anode and said cathode, such that the said four electrodes, said anode and said cathode are equally radially distributed about an axis parallel to and mid-way between said cathode and said anode.

10. A method of electrophoretic separation of molecules comprising use of an electrophoresis apparatus according to claim 3.

* * * * *